United States Patent [19]

Eggleton

[11] 4,270,388

[45] Jun. 2, 1981

[54] METHOD AND APPARATUS EMPLOYING ZERO ORDER RAMAN-NATH DIFFRACTION INFORMATION TO VISUALIZE LONGITUDINAL CHARACTER OF AN ACOUSTIC WAVE FIELD

[75] Inventor: Reginald C. Eggleton, Indianapolis, Ind.

[73] Assignee: Indianapolis Center for Advanced Research, Indianapolis, Ind.

[21] Appl. No.: 11,447

[22] Filed: Feb. 12, 1979

[51] Int. Cl.$^3$ ............................................ G01N 29/00
[52] U.S. Cl. ........................................ 73/603; 73/606
[58] Field of Search ................. 73/606, 608, 655, 657, 73/656, 603

[56] References Cited

U.S. PATENT DOCUMENTS

| | | | |
|---|---|---|---|
| 3,969,578 | 7/1976 | Mezrich et al. | 73/606 |
| 3,997,717 | 12/1976 | Mezrich et al. | 73/606 |

*Primary Examiner*—Anthony V. Ciarlante
*Attorney, Agent, or Firm*—Woodard, Weikart, Emhardt & Naughton

[57] ABSTRACT

A method and apparatus employing zero order Raman-Nath diffraction information to visualize the longitudinal character of an acoustic field. The method includes the steps of directing a first portion of a beam of coherent light at normal incidence to a reflective mirror, propogating an acoustic field within a medium to interact with the first portion of the beam, detecting signals derived from the acousto-optical interaction from which phase change and amplitude change information in the reflected zero order diffraction component of the laser beam can be derived after its return pass through the acoustic field and then generating a two-dimensional raster scan representation of the acoustic field from the detected light signals. The apparatus correspondingly includes a rigid reflective mirror, a coherent light source, an interferometer for splitting a beam from the light source into a first and a second portion and then for directing the first portion at normal incidence to the reflective mirror and intercepting at least the phase-modulated zero order diffraction component of the reflected first portion after its double pass through the acoustic field, and an optical photodetector, translator and display system for visually displaying signals derived from the phase change information in the reflected zero order diffraction component of the first portion of the beam after its passage through the acoustic field.

20 Claims, 3 Drawing Figures

METHOD AND APPARATUS EMPLOYING ZERO ORDER RAMAN-NATH DIFFRACTION INFORMATION TO VISUALIZE LONGITUDINAL CHARACTER OF AN ACOUSTIC WAVE FIELD

BACKGROUND OF THE INVENTION

This invention relates to the field of acousto-optical interaction and, particularly, to a new method and apparatus for utilizing the phase change information and the stronger signal level of the zero order of diffracted light to visualize the longitudinal characteristics of acoustic fields.

The field of acousto-optical research has greatly burgeoned in recent years as the use of ultrasound information has found a great many new and important applications in medical and other areas. With this heightened interest has also come the realistic need to more fully understand the interaction of acoustic wave energy with bodily tissues and with other objects and materials in general. To aid in this work, the need has also heightened to be able to accurately and completely visualize sound fields both in their natural state and when interfaced with objects of varied dimension and material.

As examples of work in this area, Whitman, U.S. Pat. No. 3,633,407, discloses a sound field detection principle involving the displacement of a flexible pellicle surface $P_1$ analogous to the RCA Sonovision system described below. The Whitman device is similar in technique to that used in the acoustic microscope as is the system shown in Ernvein, U.S. Pat. No. 3,829,827. The Ernvein patent discloses a typical holographic technique using a liquid surface for the acoustic image detection.

In like regard, Gabor, U.S. Pat. No. 3,745,814, and Korpel, U.S. Pat. No. 3,706,965, disclose acousto-optical surface detection systems somewhat similar to the RCA system and the Sonoscan microscope. Erikson, U.S. Pat. No. 3,990,296, and Brenden et al., U.S. Pat. No. 3,683,679, on the other hand, disclose somewhat analogous acoustic imaging systems also relying upon surface modulation to achieve the ultimate image. In this regard, Brenden et al. describes the interaction of two coherent beams on an object 79 at position 99 within a cell 15. The particles in the cell are caused to have local changes in density thereby producing diffraction, but the system lacks any phase-sensitive detector to display this information.

Mezrich et al., U.S. Pat. No. 3,997,717, is the RCA Sonovision system first developed at the Princeton Laboratories for use in acousto-optical investigation. The system was designed for visualizing transverse sections of acoustic wave fields and contains a scanning Michelson interferometer which measures the displacement of a thin, transparent metallized pellicle. The principle of the system is clear. An acoustic wave field is propogated through a medium and impinges at normal incidence on the back of the pellicle surface thereby establishing a standing wave field and theoretically causing the pellicle to respond as a particle of the medium to the acoustic field propogating through it. The Michelson interferometer provides a means for measuring the displacement of the pellicle surface in the standing wave field including a laser light source producing a beam first split into a reference and a target portion. The target portion impinges the flexible pellicle surface and the two portions are then later recombined and detection made of the change in path length of the target portion caused by the oscillating pellicle surface. The variations in path length are then used to detect the phase change information embodied in the interference pattern between the two beam portions. Mezrich et al. ('717) further theorize that the acousto-optical interaction between the ultrasonic field passing through the pellicle and the laser light portion measuring the pellicle displacement is insubstantial and does not significantly interfere with the displacement measurements.

Mezrich et al., U.S. Pat. No. 3,969,578, and Green, U.S. Pat. No. 3,716,826, are both forerunners of this RCA Sonovision system. Mezrich et al. ('578) also describes the use of the Michelson interferometer with a wiggling mirror as the means for varying the optical path length of the reference beam portion thereby providing a means of stabilizing the interferometer readings. Green discloses a similar but earlier system. As with Mezrich et al. ('717), however, both patents rely upon the physical measurement of the changes in path length of the laser light caused by the displacement of a flexible pellicle surface insonified from the back by a standing wave front as the basic principle of their sound field detection systems.

For the measurement and investigation of longitudinal wave information, systems utilizing Schlieren optics have been used for several years to study the performance of transducers and other ultrasonic devices. The principle underlying these systems is the use of first order diffracted light after acoustic interaction with a wave field in a transparent medium. A light source is used to transmit a coherent beam through a propogating acoustic wave field, or phase gradient. The beam is thereby diffracted into various orders (light components) and once through, the zero order is intercepted with a stop allowing the higher order acoustically diffracted component to be viewed. Although there is information in both phase and amplitude, the Schlieren technique then uses only the amplitude information, i.e., intensity, of the higher order diffracted light components to visualize the longitudinal character of the acoustic field. It totally disregards both the phase change information in the higher order components as well as the amplitude and phase change information in the zero order.

In this regard, Bhuta et al., U.S. Pat. No. 3,836,950, discloses a method utilizing acousto-optical interaction similar to the Schlieren technique. By positioning an apertured opaque mask 38 behind the lens 26a, the mask is able to intercept both the transmitted light-beam carrier and one first order diffracted side band component. Only the one remaining first order side band is thereby allowed to pass through the aperture in the mask for detection and imaging purposes. The system has no instrumentation for phase detection and relies solely on the amplitude of this single first order diffracted component to produce the acousto-optical image.

Alder, U.S. Pat. No. 3,431,504, describes a Bragg diffraction cell used to deflect a laser light beam as the interacting acoustic frequency is varied. The system then selects the desired diffracted order of the transmitted and deflected light pattern for subsequent translation and demodulation by the apparatus. The underlying purpose of the system is not at all concerned with investigation and visualization of sound fields as in the above-described prior art. Instead of attempting to describe the acoustic field, the Adler patent attempts to solely deflect the transmitted laser light and thereby modulate the angle of such light with a propogating acoustic beam. Moreover, this modulation of the angle does not occur with the zero order component.

As the field of ultrasound rapidly expands in the diagnostic, therapeutic, research and other areas, so too does the need for more accurate and sensitive methods and equipment for studying the acousto-optical interactions. In this regard the Schlieren imaging technique described above is hard-pressed to meet these ever-increasing demands. Relying solely upon the amplitude information of the diffracted first order light component to visualize the acoustic field, the system is lacking in the sensitivity and versatility required both for present and future applications. The need therefore exists for a new and improved system for visualizing the longitudinal and total character of acoustic wave fields being sufficiently sensitive and versatile to adapt to both present-day and future requirements.

In this regard, none of the above-cited references utilize zero order Raman-Nath diffraction to visualize the longitudinal or other characteristics of acoustic wave fields. In fact, the Adler reference specifically excludes the zero order component from the group of "orders" desirable for selection and examination. The same is true in Whitman and Bhuta et al.

SUMMARY OF THE INVENTION

One aspect of the present invention comprises a method employing zero order diffraction information to visualize the longitudinal character of an acoustic field, comprising the steps of directing a first portion of a beam of coherent light at normal incidence to a rigid reflective surface from in front thereof, propogating an acoustic field to interact with the first portion of the beam, detecting signals derived from the phase change information in the reflected zero order diffraction component of the first portion of the beam after its double pass through the acoustic field, and generating a two-dimensional representation of the acoustic field from the detected signals.

The above method constitutes a significant improvement over the Schlieren and other methods presently used for visualizing the longitudinal character of acoustic fields. Instead of solely relying upon the amplitude of the first order diffracted light component after a single pass through the acoustic wave field, the method of the present invention utilizes the phase change information in the much more intense zero order component. In addition, in the preferred embodiment, the sample zero order component is passed twice through the propogating acoustic wave field, or grating, thereby significantly increasing the magnitude of the phase change information to be sampled. This provides inherent improvements in the signal-to-noise ratio and the sensitivity of the method thus far exceeds that of the Schlieren technique. It also eliminates the measurement of changes in path length and the dependence upon flexible pellicle response and thereby the sensitivity to vibrational noise from the environment and extraneous acousto-optic interaction existing in the present-day RCA Sonovision system for visualization of transverse sections of acoustic beams.

A second aspect of the present invention comprises an apparatus to perform the above method, including a rigid reflective surface, means for producing a coherent light beam and for directing a first portion of the beam at normal incidence to said reflective surface, means for propogating an acoustic field to interact with the first portion of the light beam, and means for detecting signals derived from the phase change information in the reflected zero order diffraction component of the first portion of the light beam after its double pass through the acoustic field, and means for generating a two-dimensional representation of the acoustic field from the detected signals.

As with the described method, the above apparatus also constitutes a significant improvement over present-day systems employing Schlieren or other techniques to visualize the longitudinal character of acoustic wave fields. The displacement and measurement of a flexible pellicle surface is not required and the use of phase change information from the more intense zero order diffraction component of the beam provides significantly improved sensitivity capable of meeting the needs of today and of the future.

One mode of practicing this apparatus is to provide a modified version of the RCA Sonovision system disclosed in the Mezrich et al. ('717 and '578) references. The system includes a laser light source and a scanning Michelson interferometer including a beam splitter capable of directing and handling both the reference and target portions of the beam, a wiggling reference mirror and a form of photodetector and visual translating means for intercepting the reflected zero order diffraction component and detecting the phase change information embodied in the interference pattern of the recombined reference and target portions of the beam. Visual display information, also similar to that in the Mezrich et al. references, can then be provided by a cathode ray tube display and other means to visualize this phase change information in the form of an image representing the longitudinal character of the acoustic field. Two important redesign features, as further discussed herein, are that the laser source and sound source are both disposed 90 degrees from their positions in Mezrich et al. ('717 and '578) in order that: (1) the target portion of the beam leaving the beam splitter corresponds to Raman-Nath scattered, or diffracted, light; and (2) the sound field is propogated in front of the rigid reflective surface to interact with the first or target portion of the light beam.

A still further advantage which accrues to the above embodiments of the present invention is the potential for use of pulsed ultrasound in combination with time gates to eliminate certain undesirable and confusing parts of the acoustic field and thereby provide for complete visualization of scattering phenomena from various acoustic targets, all as further discussed hereinbelow.

One object of the present invention is to provide an improved method and apparatus for visualizing the longitudinal character of acoustic beams.

Another object of the present invention is to provide a method and apparatus for sampling at least the phase change information embodied in zero order Raman-Nath diffracted light for the purpose of detecting and displaying the longitudinal character of acoustic beams.

A third object of the present invention is to provide an method and apparatus for visualizing the longitudinal character of acoustic beams of significantly improved sensitivity and versatility in order to meet both the present and future needs for investigation in the area of acousto-optical interaction.

Related objects and advantages of the present invention will be apparent from the following description.

DESCRIPTION OF THE PREFERRED EMBODIMENT

Figure 1:
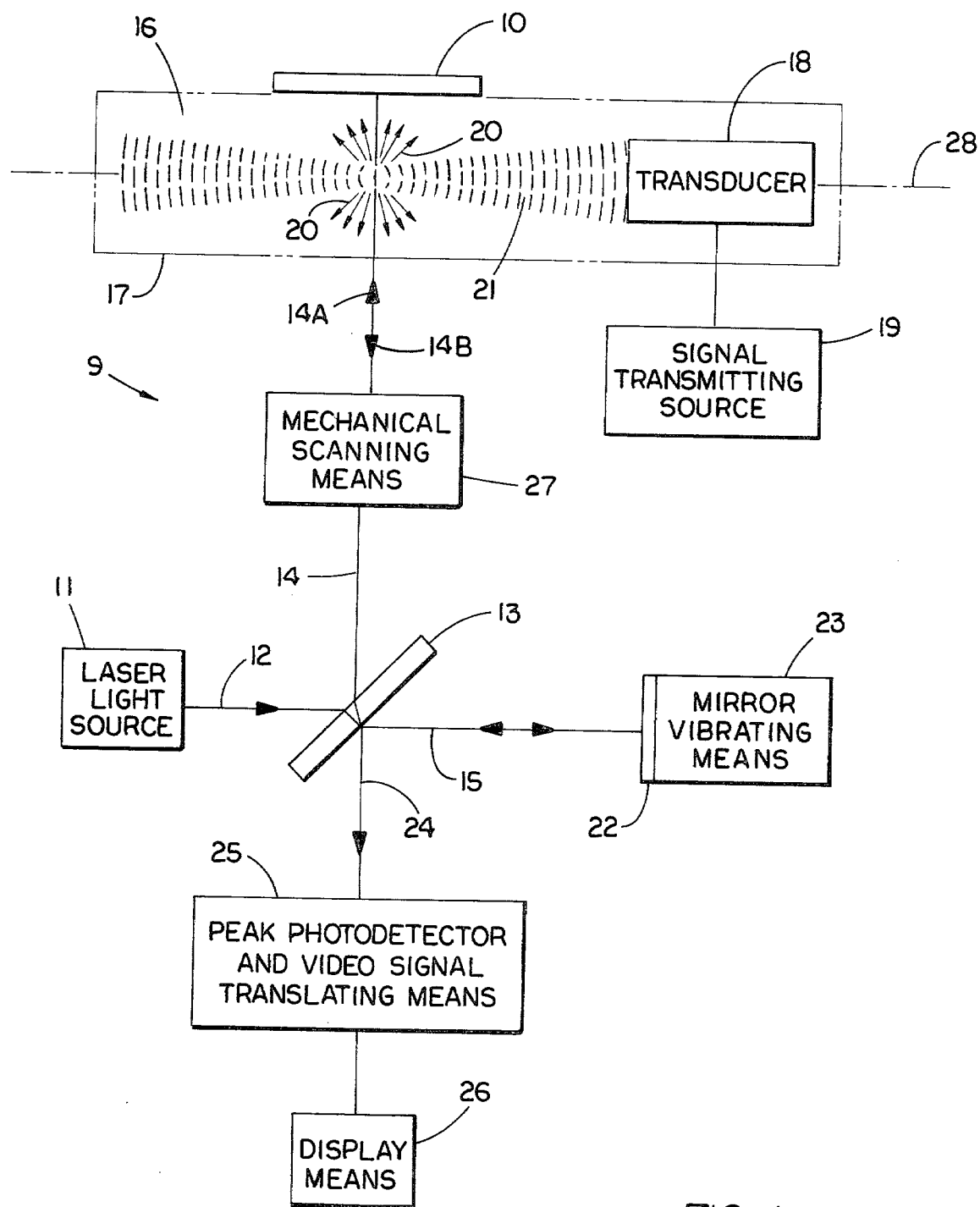
FIG. 1 is a block diagram of the preferred system of the present invention.

As discussed above, one aspect of the present invention comprises a system, or apparatus, employing zero order Raman-Nath diffraction information to visualize the longitudinal character of an acoustic field, an example of which is depicted in FIG. 1. For the purposes of this application, and of the claims attached hereto, "Raman-Nath diffraction" is used to define a form of acousto-optical interaction based upon the Raman effect which can be described as the scattering of light from a gas, liquid, or solid with a shift in wavelength (phase) from that of the usual incident radiation. It is a scattering, or diffraction, method usually studied at right angles to the sound field and requiring an optical arrangement similar to that depicted in FIG. 1.

Specifically, in "Raman-Nath diffraction," a beam 12 of coherent light from a laser source 11 first impinges on a beam splitter where it is split. A reference portion of the beam, corresponding to second portion 15 described herein, is unscattered and passes directly through the splitter where it is then returned by means of a reflective mirror 22. Another portion of the beam, corresponding to first portion 14 described herein, is reflected or diffracted at a right angle to the initial beam by the beam splitter. This scattered portion passes through the sound field to be studied where it undergoes a change in phase and is then collected for analysis.

Also for the purposes of this application, the "first or target portion of the light beam" is used to define this Raman-Nath light portion scattered at a right angle to the original beam and directed at normal incidence to the rigid reflective surface 10. As this Raman-Nath scattered light 14A passes through the interposed sound field, it is diffracted producing zero, first, second and higher orders of diffracted light components 20. The zero order component is reflected by the mirrored surface and passes back through the sound field along the same path 14B, at which time similar ordered diffraction occurs. The method and apparatus of the present invention employ this selected zero order Raman-Nath diffracted light component remaining after the return, or double, pass through the acoustic field to visualize the longitudinal character of the field itself. For the portion of the acoustic spectrum normally employed in medicine and industry, the Raman-Nath theory has been found to provide the most applicable description of light diffraction by acoustic fields.

With this in mind, the system, or apparatus, 9 of the preferred embodiment first includes a rigid reflective surface such as, for example, mirror 10 in FIG. 1.

Second, means is provided for producing a coherent light beam 12 and for directing a first portion of the beam at normal incidence to the reflective surface. In the preferred embodiment, the means for producing constitutes a laser light source 11, such as a He-Ne gas laser, which upon activation emits a coherent and monochromatic light beam 12 at a predetermined or known wavelength. The means for directing of the preferred embodiment includes a beam splitter 13 which initially splits the light beam 12 into a first, or target, portion 14 and a second, or reference, portion 15 as further discussed hereinbelow.

Third, means is provided for propogating an acoustic field 21 between the reflective mirrored surface 10 and this means for producing and for directing to interact with the first portion 14 of the light beam 12. The acoustic field 21 of preferred system 9 is further propogated parallel to this reflective mirrored surface 10 and at normal incidence to the light beam 14. This is accomplished by first establishing a liquid medium 16, preferably water, within an enclosure 17 immediately in front of reflective mirror 10. A suitable transducer 18 is then anchored within the medium at the proper direction, i.e., parallel to surface 10, and is operably connected to an ultrasonic pulse generator, frequency driver or other appropriate signal-transmitting source 19. These transducers and ultrasonic signal sources are well known in the art and maintain little significance with respect to the present invention.

Next required is means for detecting signals derived from the phase change information in the reflected zero order diffraction component of the first portion 14 of the light beam after its return pass through the acoustic field 21. In this regard, the several first, second and higher order diffracted components of first portion 14 are generally represented by numeral 20 in FIG. 1.

One theory underlying the present invention is that the presence of a sound field in a medium induces changes of density which cause local changes of the optical index of refraction within the medium. A phase grating is thereby produced within the liquid medium capable of diffracting light passing therethrough. This acousto-optical interaction is strongest if the light and sound beams are maintained at right angles, i.e., at normal incidence to one another.

In the Raman-Nath theory, the liquid medium through which the sound is propogating establishes a grating which modulates, or changes, the phase speed of the traveling light. It is possible to mathematically show through formula deviation the exact relationship between the acoustic pressure in the medium, the phase length of interaction and the phase change, or modulation, of the light propagating through the grating.

An interferometer is a device known to be useful in measuring lengths or changes in phase due to the velocity changes with great accuracy by counting the number of interference fringes or fractions of a fringe that pass by the field of view caused by a recombined reference and target beam. See D. Halliday and R. Resnick, *Physics Parts I and II* 43-7 (1966). For example, in Mezrich et al. ('717 and '578) a Michelson interferometer is used to measure changes in path length caused by displacement of the vibrating pellicle surface by means of peak phase interference.

Unlike Mezrich et al. ('717 and '578), no changes in path length caused by an insonified and vibrating surface are measured herein to visualize the longitudinal character of an acoustic field. Instead, the interferometer means is used in the present embodiments to measure changes in light velocity caused by the acoustic field and to then detect signals derived from this phase change information and to thereby measure the peak phase change, or modulation, of the reflected zero order diffraction component. Means 25 is then provided to translate these detected signals and to generate therefrom a two-dimensional representation on a C.R.T., i.e., cathode ray tube, or other appropriate display means 26. This information or raster scan finally displayed on the C.R.T. is known to correspond substantially to the varying densities within the phase grating and thereby provides an accurate depiction of the longitudinal character of the acoustic field at the point of acousto-optic interaction.

In preferred system 9, a modified version of the RCA Sonvision system described above and disclosed in detail in the Mezrich et al. ('717 and '578) patents is used to provide the means for directing the beam portions and the means for detecting and then for generating a two-dimensional representation using the signals derived from this phase change information. This Sonovision system is well suited for displaying zero order Raman-Nath diffraction images because of the built-in Michelson interferometer which is employed to detect pellicle displacement and thus changes in path length by measuring the peak phase change, or modulation, produced in the optical pathway of the target beam. It is capable of detecting displacements as small as a fraction of an angstrom and has good dynamic range capability. Furthermore, although not previously understood or appreciated, it can also measure changes in the speed of light produced by local changes in density induced by the sound field. For these reasons, both Mezrich et al. ('717 and '578) patents are hereby expressly incorporated herein by reference as to all features and disclosure used herein or having reference or application hereto.

Figure 2:
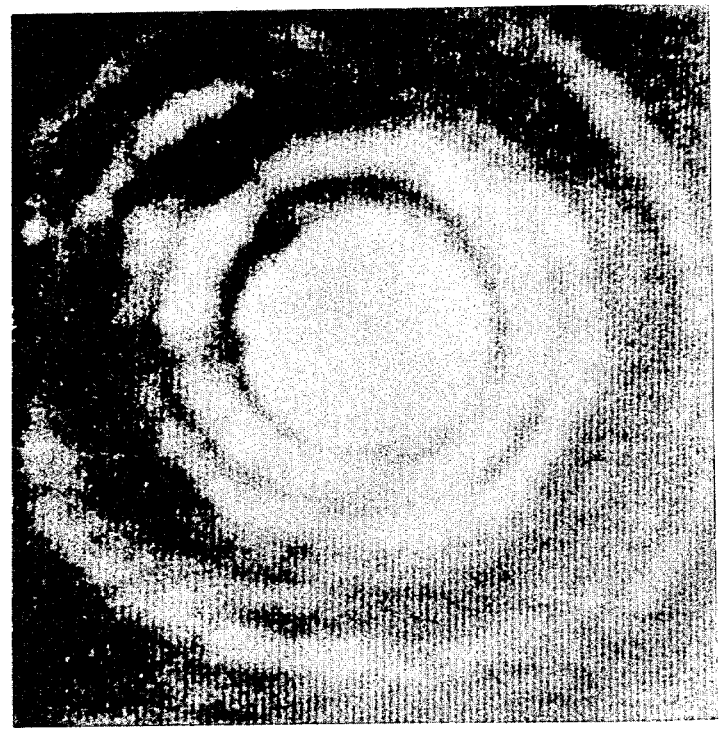
FIG. 2 is a two-dimensional representation of the transverse character of an acoustic field generated using the system disclosed in the Mezrich et al. references.
Figure 3:
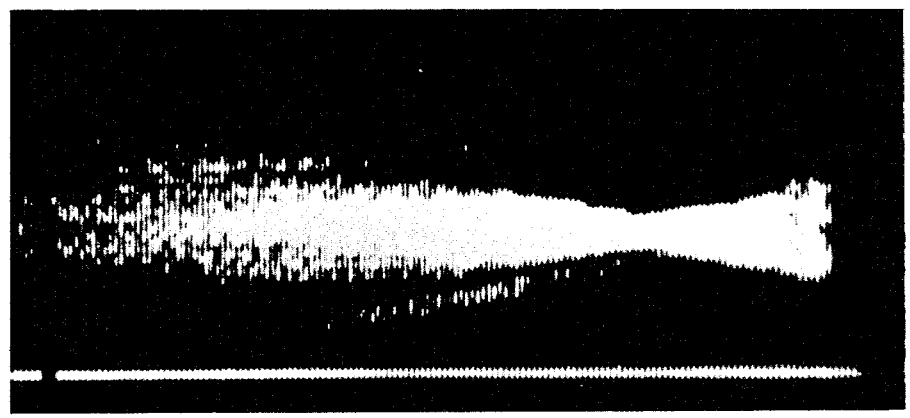
FIG. 3 is a two-dimensional representation of the longitudinal character of an acoustic field generated using the preferred system in FIG. 1.

In this regard, FIG. 2 shows a two-dimensional representation 31 of the transverse character of an acoustic wave system and is typical of the images obtained using the RCA Sonovision. In contrast, FIG. 3 shows a two-dimensional representation 32 of the longitudinal character of an acoustic field and is a typical example of a representation generated using preferred system 9 of the present invention.

As to specific modifications of this Sonovision system for the present application, the flexible pellicle is replaced by a rigid mirror 10 which provides an inherently more stable reflective surface than the vibrating pellicle. The sound source is transposed 90 degrees so the acoustic field to be visualized is then propagated in front of the target mirror 10 to interact with the interrogating portion 14A of the laser beam 12. As described above, and depicted in FIG. 1, the light source has also been transposed 90 degrees to emit a beam parallel to the mirror 10 so the scattered first, or interrogating, portion 14A of the beam corresponds to the Raman-Nath light component. The sound field then creates a phase grating in the medium which produces the diffraction of the laser light. The resulting modulation of the velocity of this light by the local changes in pressure and density produces corresponding changes in the phase of the reflected zero order diffracted light component entering the interferometer and has an effect similar to the phase shift produced by the pellicle displacement and changing path length in Mezrich et al. ('717 and '578).

As depicted in FIG. 1, preferred system 9 of the present invention includes a laser light source 11 emitting a single beam 12 impinging upon a beam splitter 13. Similar to the Mezrich et al. references, the beam splitter directs a portion 14 of the original beam through the acoustic field at normal incidence to the rigid mirror 10.

A second reference (light) component 15 is directed by the splitter 13 at normal incidence to a rigid reference mirror 22. Mirror 22 is continuously vibrated at a predetermined frequency significantly lower than the known frequency of the propagated acoustic field 21 by means of an appropriate mechanical vibrator, such as a piezoelectric vibrator, or an electro-optic crystal modulator represented by box 23 in FIG. 1. The amount of this vibrating, or wiggling, is such that the total round-trip optical path length of second portion 15 is varied by an amount greater than one-half the wavelength of the coherent light beam 12, all as specifically disclosed in detail in the Mezrich et al. patents incorporated herein by reference.

On its return pass through the acoustic field 21, the now phase- and intensity-modulated first portion 14B of the original beam corresponding to the reflected zero order diffraction light component is recombined at the beam splitter 13 with the second reference portion 15 of the original beam. This recombined beam 24 is then transmitted to the means described above for detecting signals derived from the phase change information in the reflected zero order diffraction component of the first portion of the light beam.

In preferred system 9, utilizing the modified Ultra Sonovision system in Mezrich et al. ('717 and '578), this detection is accomplished by measuring the peak interference fringes or fractions of a fringe of the first and second portions of the recombined beam 24. As stated in both Mezrich et al. patents, it is known in interferometry that the instantaneous amplitude of the recombined and interfering light portions sensed by the peak photodetector and video signal translating means depends on the phase difference between the two light components at that instant of time. Utilizing the peak voltage indicator and the peak photodetector and video signal translating means of Mezrich et al., represented by box 25 in FIG. 1, a video signal output is produced which corresponds to the peak phase changes caused by the acoustic field at the location scanned by the first portion 14 of the light beam. This video signal output is then employed to intensity modulate the electron beam of a C.R.T. or other appropriate display means, represented by box 26 in FIG. 1. The resulting generated image depicts a two-dimensional representation of the instantaneous longitudinal character of the acoustic field embodied within the detected signals derived from the phase change information in the reflected zero order diffraction light component.

A mechanical scanning means 27 is also provided in preferred system 9 to allow exploration of each point on the acoustic field projected on the plane or area scanned. The need for this mechanical scanning feature, of course, depends upon the initial character of "light beam 12" which properly contemplates within its scope a "light beam" generating a point, line or two-dimensional area when viewed in axial cross-section. But regardless, this scanning enables the system to give absolute sound field calibration readings if the transducer is rotated about its axis 28. The signals derived then generate a two-dimensional representation of the scanned acoustic field for display on a C.R.T. or other monitor represented by box 26. A scan converter (not shown) may also be utilized in scanning means 27 to store the derived signals during the scanning phase thereby allowing two-dimensional images to be stored and displayed, or digitized for computer processing, representing complete longitudinal scans of the transducer field using the zero order Raman-Nath diffraction technique. These mechanical scanners and scan converters are known and available in the art, and the particular scanner or converter used has little significance to the present invention.

The above embodiment provides much versatility in studying the longitudinal character of acoustic beams. As in Mezrich et al. ('717 and '578), objects of varying shape, density and material can be used as acoustic target elements and placed within the sound fields to enable detailed studies of the effect of such objects on sound propogation and its characteristics.

Furthermore, an advantage which accrues to the preferred embodiments of the present invention is the potential for use of pulsed ultrasound coupled with time gates to eliminate certain undesirable and confusing parts of the acoustic field. This is unlike Mezrich et al. ('717 and '578) which requires a continuous wave field impinging upon the pellicle surface to establish a uniform pellicle vibration.

For example, to examine the back scattering from an acoustic target (not shown) positioned to interact with the sound field, the present system can be made insensitive to the acoustic field propagating to the target and can examine only that pulsed field which is reflected from the target. This can be accomplished by controlling the interposition, i.e., opening and closing, of an electrically or mechanically operated time gate between the acoustic source and the target to correspond to the time during which the reflections occur. This principle may be utilized to examine the acoustic field scattered by a target in a manner which would be impossible by the Schlieren method. These time gates and the circuitry and linkage required for their installation and use are known and available in the art, and contribute no inventive aspect by themselves to the embodiments described herein.

Although other methods have been employed to look at back scattering from an acoustic target, no other method has provided a means for examining the simultaneous scattering throughout 360 degrees of the longitudinal plane around the target as is potentially available with the present embodiments. These other available methods either uniformly impose a limitation on possible inspection based upon the finite aperture required for the systems to operate or, as is the case in the Schlieren system, the forward propagating beam obscures the back scattered beam thereby eliminating the visualization of back scattering altogether. The preferred embodiments of the present invention, modified as indicated herein, solve these problems and provide for greater versatility through the potential for use of this pulsed mode ultrasound.

Another feature also lending versatility and sensitivity to the above embodiment is that it may be possible to make further use of the more intense amplitude (improved signal-to-noise ratio) information characteristic of the zero order Raman-Nath diffracted light in generating two-dimensional representations of acoustic fields. Such further uses are clearly both within the contemplation and scope of the present invention and within the knowledge and skill of one of ordinary skill in the art well versed with applicant's invention as disclosed herein.

As further described above, a second aspect of the present invention comprises a method employing zero order diffraction information to visualize the longitudinal character of an acoustic field. The preferred embodiment of this method first comprises the step of directing a first portion of a beam of coherent light at normal incidence to a rigid reflective surface, such as mirror 10 in FIG. 1, from in front thereof.

The next step comprises propogating an acoustic field to interact with the first portion of the beam. This propogating sets up, or establishes, a phase grating for the diffraction study. The third step then comprises detecting signals derived from the phase change information in the reflected zero order diffraction component of the first portion of the beam after its return, or double, pass through the acoustic field. The fourth step comprises generating a two-dimensional representation of the acoustic field from the detected signals.

The preferred method of the present invention is accomplished by means of the system, or apparatus, 9 described in detail hereinabove. Accordingly, the propogating step further includes establishing an enclosure 17 containing a liquid medium 16, such as water, in front of and parallel to the rigid mirror 10 and then activating a properly positioned transducer 18 with an ultrasonic generator or other appropriate means 19.

In the preferred method, the directing, detecting and generating steps are then performed by means of the interferometer and display system described above, and constituting a modified version of the RCA Sonovision system disclosed in detail in the Mezrich et al. patents incorporated herein by reference. The directing step first involves splitting the beam 12 into a first and a second portion 14 and 15 and then impinging these portions on the mirror 10 and a wiggling reference mirror 22, respectively. Next, recombining of the second portion 15 and the first portion 14, which now corresponds to the phase-modulated zero order diffraction component of the light, is also accomplished by the beam splitter 13.

Detecting signals derived from the phase change information in the reflected zero order diffraction component is accomplished by interferometrically sensing and measuring the instantaneous amplitude of the recombined and interfering light portions, this amplitude being known to correspond to the peak phase difference between the portions 14 and 15 at that instant of time. This information is then translated into a video signal output and visually displayed as a two-dimensional representation by use of the photodetector and video signal translating and display means 25 and 26 previously described. The displayed image or representation corresponds to the longitudinal character of the acoustic field 21 at the location and instant of acousto-optic interaction.

Another step in the preferred method comprises scanning the acoustic field during the directing and detecting steps in order to obtain phase change information on all aspects of the sound field. The visual displaying of derived signals from this cumulative information can then be either continuous or delayed. But regardless, it will provide a two-dimensional representation of the complete longitudinal character of the transducer field for the purpose of further reasearch and study.

Although the preferred embodiments described in detail herein employ various of the components and steps in the RCA Sonovision system disclosed in the Mezrich et al. patents, it is clear that other components and means are known and available in the art to perform the same, or similar, individual functions of scanning, detection and display. These are accordingly expressly within the contemplation and scope of the present invention and of the claims attached hereto.

Furthermore, while the invention has been illustrated and described in detail in the drawing and foregoing description, the same is to be considered as illustrative and not restrictive in character, it being understood that only the preferred embodiments have been shown and described and that all changes and modifications that come within the spirit of the invention are desired to be protected.

What is claimed is:

1. A method employing zero order diffraction information to visualize the longitudinal character of an acoustic field, comprising the steps of:
   (a) directing a first portion of a beam of coherent light at normal incidence to a rigid reflective surface from in front thereof;
   (b) propogating an acoustic field to interact with the first portion of the beam;
   (c) detecting signals derived from the phase change information in the reflected zero order diffraction component of the first portion of the beam after its double pass through the acoustic field; and
   (d) generating a two-dimensional representation of the acoustic field from the detected signals.

2. The method of claim 1 in which said propogating includes establishing an acoustic phase grating within an enclosed liquid medium to intercept the first portion of the beam.

3. The method of claim 2 in which said directing includes the steps of:
   (a) splitting the beam into a first portion and a second portion;
   (b) directing the first portion at normal incidence to the reflective surface from in front thereof; and
   (c) directing the second portion at normal incidence to a rigid reference mirror.

4. The method of claim 3 in which said detecting includes the steps of:
   (a) recombining the reflected second portion and the reflected zero order diffraction component of the first portion of the light beam; and
   (b) measuring the interference pattern therebetween attributable to the phase change in the zero order diffraction component.

5. The method of claim 1 additionally comprising scanning the acoustic field during said directing and said detecting.

6. The method of claim 1 additionally comprising scanning the coherent light beam over the acoustic field during said directing and said detecting.

7. The method of claim 1 wherein said directing is of a first portion of a beam of coherent monochromatic light.

8. The method of claim 1 wherein said detecting is of signals derived from the amplitude and phase change information in the reflected zero order diffraction component of the first portion of the beam.

9. The method of claim 5 additional comprising varying the total round-trip optical path length of the second portion of the beam directed at the rigid reference mirror by an amount greater than one-half the wavelength of the coherent light beam, said varying including wiggling the rigid reference mirror at a frequency significantly lower than the frequency of the propogated acoustic field.

10. The method of claims 1, 2, 3, 4, 5, 6, 7, 8 or 9 wherein said propogating is at normal incidence to the first portion of the beam.

11. The method of claims 1, 2, 3, 4, 5, 6, 7, 8 or 9 wherein said propogating is of a pulsed acoustic field.

12. The method of claim 11 additionally comprising interposing an acoustic target to interact with the pulsed field and with the first portion of the beam.

13. A system employing zero order diffraction information to visualize the longitudinal character of an acoustic wave field comprising:
   (a) a rigid reflective surface;
   (b) a coherent monochromatic light source;
   (c) means for directing a first portion of a beam emitted from said light source at normal incidence to said reflective surface;
   (d) an acoustic field propogated within a medium and before said reflective surface to interact with the first portion of the light beam;
   (e) means for scanning said acoustic field with the first portion of the beam emitted from said light source;
   (f) means for detecting signals derived from the phase change information in the reflected zero order diffraction component of the first portion of the light beam after its return pass through said acoustic field; and
   (g) means for generating a two-dimensional representation of acoustic field from the detected signals.

14. An apparatus employing zero order diffraction information to visualize the longitudinal character of an acoustic wave field comprising:
   (a) a rigid reflective surface;
   (b) means for producing a coherent light beam and for directing a first portion of the beam at normal incidence to said reflective surface;
   (c) means for propogating an acoustic field to interact with the first portion of the light beam;
   (d) means for detecting signals derived from the phase change information in the reflected zero order diffraction component of the first portion of the beam after its return pass through the acoustic field;
   (e) means for generating a two-dimensional representation of the acoustic field from the detected signals.

15. The apparatus of claim 14 additionally comprising means for scanning the acoustic field with the first portion of the light beam.

16. The apparatus of claim 14 in which said means for propogating includes a liquid medium contained within an enclosure, a transducer, and an ultrasonic generator means operably connected to said transducer for propogating an acoustic beam therefrom.

17. The apparatus of claim 16 in which said means for detecting includes an interferometer, said interferometer further including a beam splitter and a rigid reference mirror with wiggling means operably connected thereto, said means for directing including means for directing a second portion of the beam split at said beam splitter at said rigid reference mirror, said wiggling means being for varying the total round-trip path length of the second portion of the beam by an amount greater than one-half the wavelength of the coherent light beam and at a frequency signficantly lower than the frequency of the propogated acoustic field.

18. The apparatus of claims 14, 15, 16 or 17 wherein said propogating means is for propogating an acoustic field at normal incidence to the first portion of the beam.

19. The apparatus of claims 14, 15, 16 or 17 wherein said propogating means is for propogating a pulsed acoustic field.

20. The apparatus of claim 19 additionally comprising an acoustic target interposed to interact with the pulsed field and with the first portion of the beam.

* * * * *